United States Patent

Ho et al.

(10) Patent No.: US 7,556,043 B2
(45) Date of Patent: Jul. 7, 2009

(54) PATIENT INTERFACE WITH AN INTEGRAL CUSHION AND NASAL PILLOWS

(75) Inventors: Peter Chi Fai Ho, Pittsburgh, PA (US); Jian-An Jiang, Shezhen (CN); Hai-Yan Zhu, Shezhen (CN)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/585,320

(22) Filed: Oct. 23, 2006

(65) Prior Publication Data

US 2007/0089749 A1 Apr. 26, 2007

Related U.S. Application Data

(60) Provisional application No. 60/729,516, filed on Oct. 24, 2005.

(51) Int. Cl.
*A62B 18/02* (2006.01)
(52) U.S. Cl. .............................. 128/207.18; 128/206.21
(58) Field of Classification Search ............ 128/206.11, 128/201.23, 206.12, 206.18, 206.21, 206.26, 128/206.28, 207.13, 207.18
See application file for complete search history.

(56) References Cited

U.S. PATENT DOCUMENTS

| 4,248,218 | A | * | 2/1981 | Fischer ................. 128/204.18 |
| 4,782,832 | A | * | 11/1988 | Trimble et al. ......... 128/207.18 |
| 6,119,694 | A | * | 9/2000 | Correa et al. .......... 128/207.13 |
| 6,418,928 | B1 | | 7/2002 | Bordewick et al. |
| 6,581,601 | B2 | * | 6/2003 | Ziaee .................... 128/206.21 |
| 6,651,663 | B2 | | 11/2003 | Barnett et al. |
| 7,156,096 | B2 | * | 1/2007 | Landis .................. 128/204.18 |
| D542,912 | S | * | 5/2007 | Gunaratnam et al. ..... D24/110.5 |
| 2002/0053347 | A1 | | 5/2002 | Ziaee |
| 2002/0096178 | A1 | | 7/2002 | Ziaee |
| 2005/0076913 | A1 | | 4/2005 | Ho et al. |

\* cited by examiner

*Primary Examiner*—Steven O Douglas
(74) *Attorney, Agent, or Firm*—Michael W. Haas

(57) ABSTRACT

The patient interface (10) of the present invention includes a pair of nasal pillows (28) for delivery of gas. The nasal pillows (28) project from a partition (22) that separates an interior of the patient interface into a first chamber (24) that is configured to receive the nose of a patient when the patient interface is mounted operatively on the face of the patient and into which the nasal pillows (28) project and a second chamber (26) that has a port (30) for delivery of gas to and from the nasal pillows (28) via the second chamber (26).

25 Claims, 11 Drawing Sheets

PATIENT INTERFACE WITH AN INTEGRAL CUSHION AND NASAL PILLOWS

PRIORITY CLAIM

This application claims priority under 35 U.S.C. § 119(e) from provisional U.S. patent application No. 60/729,516 filed Oct. 24, 2005 the contents of which are incorporated herein by reference.

TECHNICAL FIELD

The present invention generally relates to a patient interface for use in a pressure support system that supplies a flow of gas to the airway of a patient, and, in particular, to a patient interface that includes a support having an integral nasal cushion and integral nasal pillows.

BACKGROUND OF THE INVENTION

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), Cheyne-Stokes respiration, or congestive heart failure.

Non-invasive ventilation and pressure support therapies involve the placement of a patient interface, which is typically a nasal, nasal/oral mask, or a total face mask, on the face of a patient. The patient interface couples the ventilator or pressure support system with the airway of the patient, so that a flow of breathing gas can be delivered from the flow/pressure generating device to the airway of the patient.

Because patient interfaces are typically worn for an extended period of time, a variety of concerns must be taken into consideration. For example, in providing CPAP to treat OSA, the patient normally wears the patient interface all night long while he or she sleeps. One concern in such a situation is that the patient interface is as comfortable as possible, otherwise the patient may avoid wearing the interface device, defeating the purpose of the prescribed pressure support therapy. It is also important that the patient interface provide an adequate seal against the patient's face without discomfort. One problem that can arise is that in order for the mask to maintain a seal without any undue gas leaks around the periphery of the mask, the mask is often compressed against the patient's face with too much force, causing discomfort.

Typically, patient interfaces include a member housing shell and a cushion (also referred to as a seal or seal member) attached to the shell. The cushion contacts the surface of the patient and operates to both locate and seal the interface with the face of the patient. The member is held in place by a headgear assembly that wraps around the head of the patient. Together, the patient interface and headgear form a patient interface assembly. A typical headgear assembly includes flexible, adjustable straps that extend from the patient interface to attach the patient interface to the patient.

In addition to the patient interface described above, it is also known to have patient interfaces with nasal pillows that seal within the nares of a patient. As best appreciated with reference to FIG. 1, the nasal pillows associated with a tubular air delivery system were worn with semi-rigid or rigid headgear 102 attached to the crown of the head. More specifically, as shown in FIG. 1, prior art nasal pillows 104 are supported by a shell 106 which, in turn, is connected to a swivel 108 which, in turn, is coupled to an over-the-head hose 110 which is connected to a gas source 112. Headgear 102 attached to the crown of a patient's head secures the assembly in position to enable the delivery of a suitable breathing gas to, and from, the patient via the nasal pillows. In an alternative (not shown) to the arrangement in FIG. 1, a flexible tube strapped to the face or around the ears of the patient may replace the over-the-head hose.

Although nasal pillows have performed very well in the art, further advancements would be desirable. For instance, contemporary nasal pillows are often compressed within the nares of the patient's nose in order to form an adequate seal and properly locate the pillows on the face of the patient. In addition, it is often necessary to utilize a rather large and bulky headgear assembly to properly support and locate the patient interface. As best appreciated with reference to FIG. 1, the nasal pillows extend upward in a hook-like configuration. This configuration tends to pry the patient's nose upward which may result in discomfort for some patients. Secondly, one of the strengths of this device is that it minimized the degree of contact with the patient's face; yet, this also presents a drawback since the prying force is concentrated in a small region. Furthermore, properly orienting the device in order to affect an adequate seal may require making multiple adjustments to the headgear assembly. In addition, nasal pillows may lack the stability needed which could ultimately result in compromising the seal between the patient and the nasal pillows.

What is therefore needed, and not disclosed in the prior art, is an improved patient interface that includes nasal pillows.

DISCLOSURE OF THE INVENTION

Accordingly, it is an object of the present invention to overcome one or more of the above-noted deficiencies in the art. This object is achieved in one embodiment of the present invention with a patient interface for use by a patient that is formed as a one-piece, unitary structure which includes a member having a peripheral edge and a partition integral with the member. The partition separates an interior of the patient interface into a first chamber configured to receive a nose of a patient and a second chamber. A pair of nasal pillows are integral with the partition and project therefrom into the first chamber for full or partial insertion into the nostrils of a patient when the patient interface is mounted operatively on the face of the patient. The member includes an integral port in fluid communication with the second chamber for delivery of gas to and from the patient via the nasal pillows.

In another embodiment, the invention is a one-piece, unitary patient interface defining an interior space and a means for dividing the interior into a first chamber configured to receive a nose of a patient and a second chamber. The patient interface includes means projecting from the dividing means into the first chamber for delivery of gas to and from at least one nostril of the patient. Lastly, the patient interface includes means in fluid communication with the second chamber for delivery of the gas to and from the patient via the second chamber and the delivery means.

In yet another embodiment, the invention is a patient interface for use by a patient. The patient interface comprises a pair of projections for delivery of gas. The projections extend from a partition that separates the patient interface into a first chamber that is configured to receive the nose of a patient when the patient interface is mounted operatively on the face of the patient and into which the pair of projections extend and a second chamber that has a port for delivery of gas to and from the projections via the second chamber.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BEST MODE(S) FOR CARRYING OUT THE INVENTION

The present invention will be described with reference to the accompanying figures where like reference numbers correspond to like elements.

Figure 1:
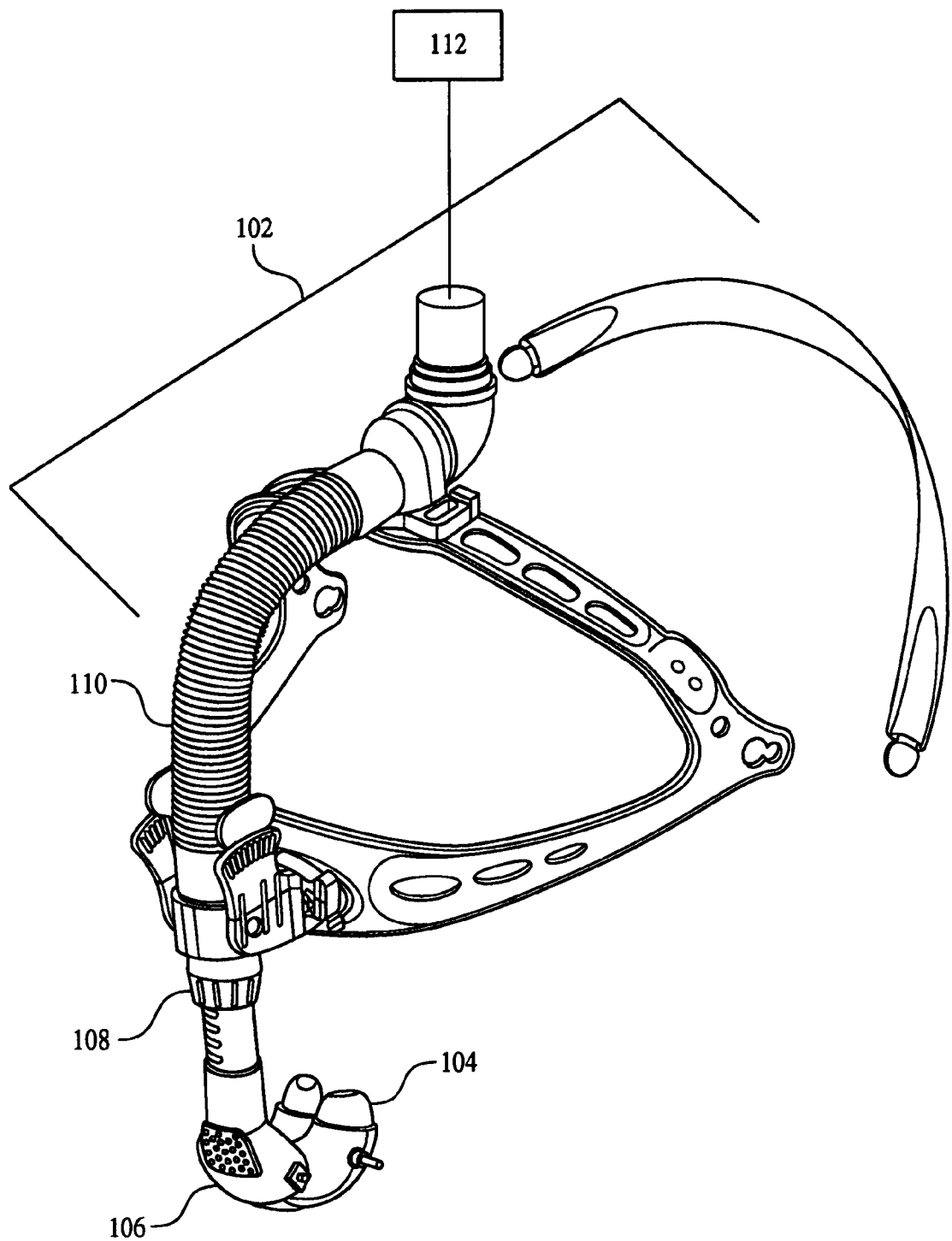
FIG. 1 is a view of prior art nasal pillows and fluid delivery system mounted operatively on a patient.
Figure 2:
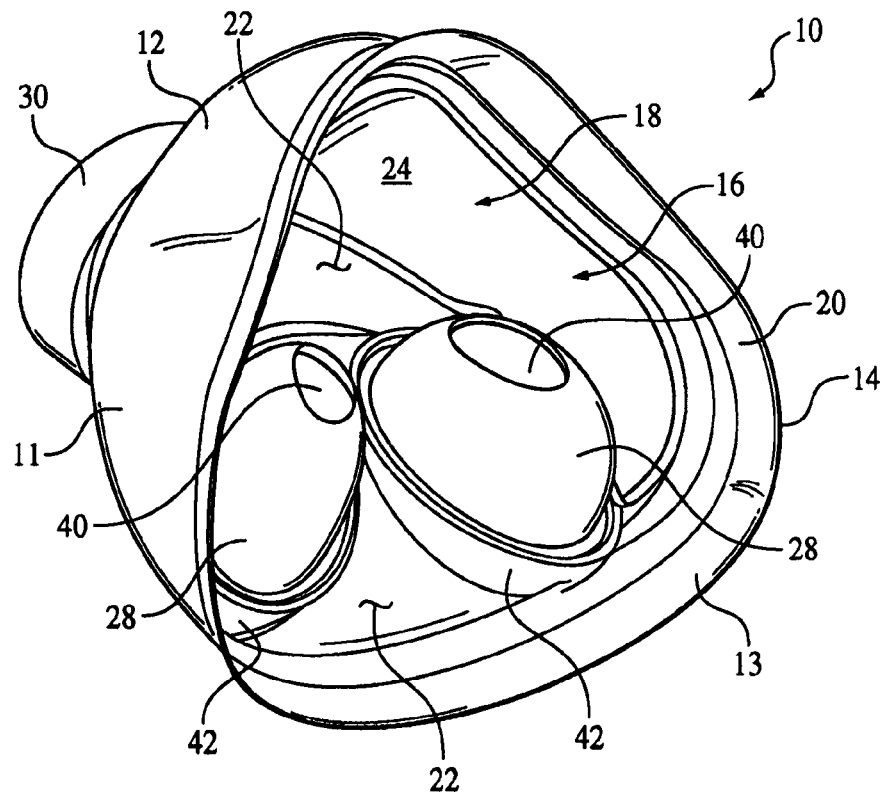
FIG. 2 is a perspective view of the open end of a patient interface in accordance with the present invention.
Figure 3:
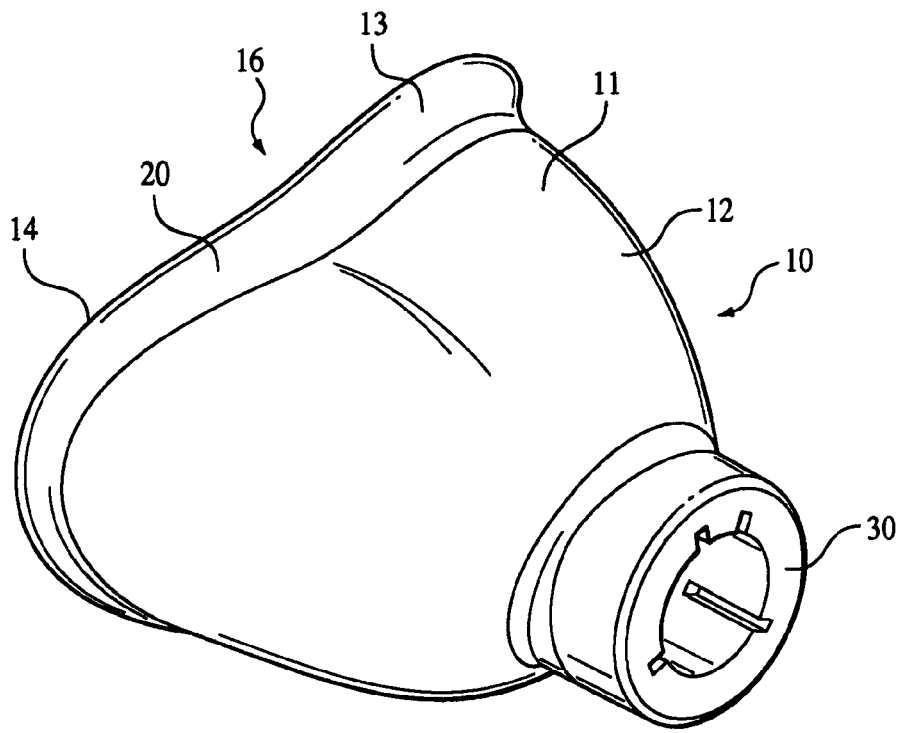
FIG. 3 is a perspective view of the exterior of the patient interface shown in FIG. 2.
Figure 4:
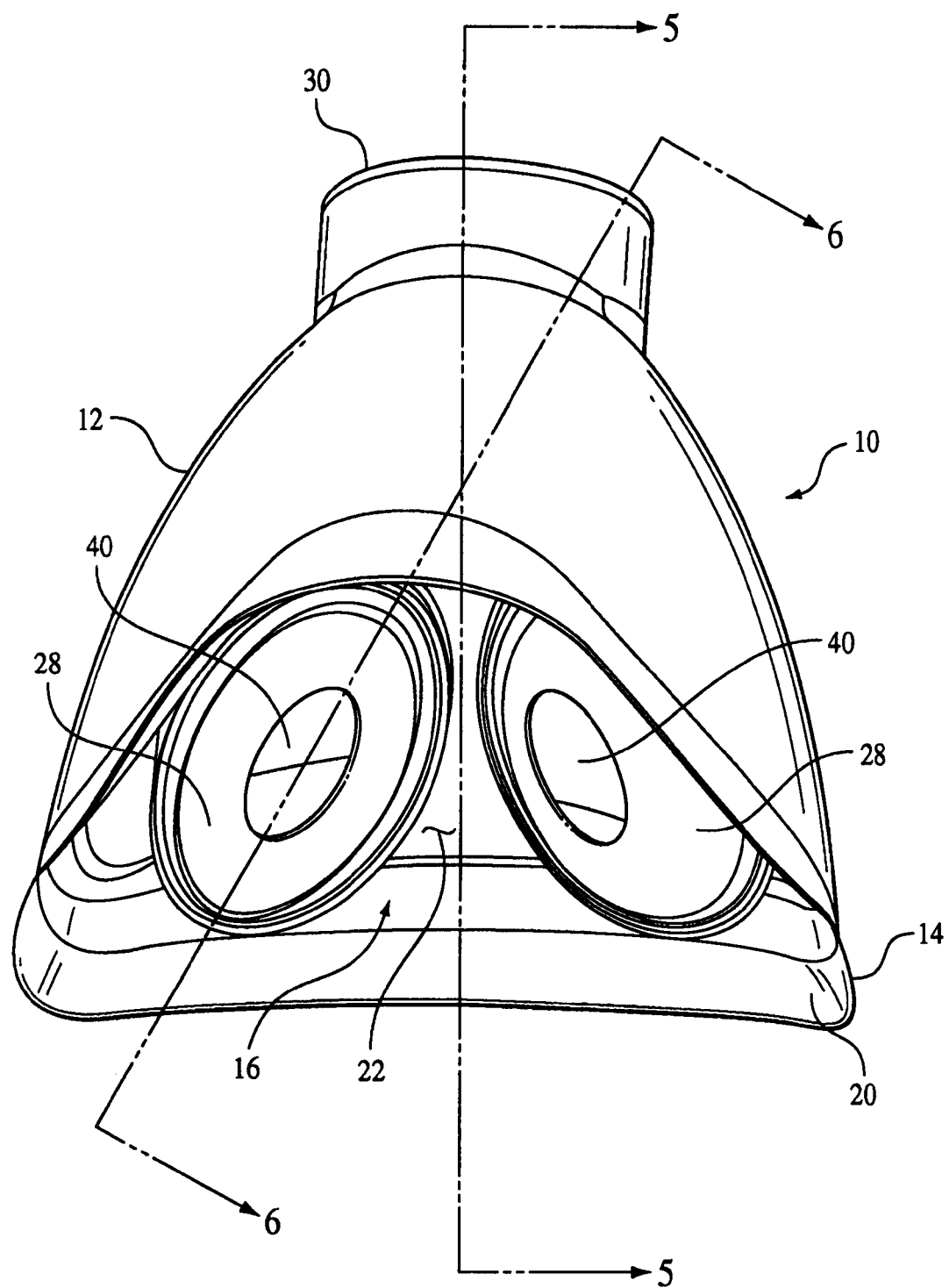
FIG. 4 is a top view of the patient interface shown in FIG. 2.

With reference to FIGS. 2-4, the present invention relates to a patient interface 10 comprising a member 11 having a shell portion 12 and a cushion portion 13 with a peripheral edge 14 surrounding an opening 16 into an interior 18 of patient interface 10. The cushion 13 includes a flange 20 that, in the illustrated embodiment, flares outwardly away from interior 18 to provide additional clearance within the interior 18.

Figure 5:
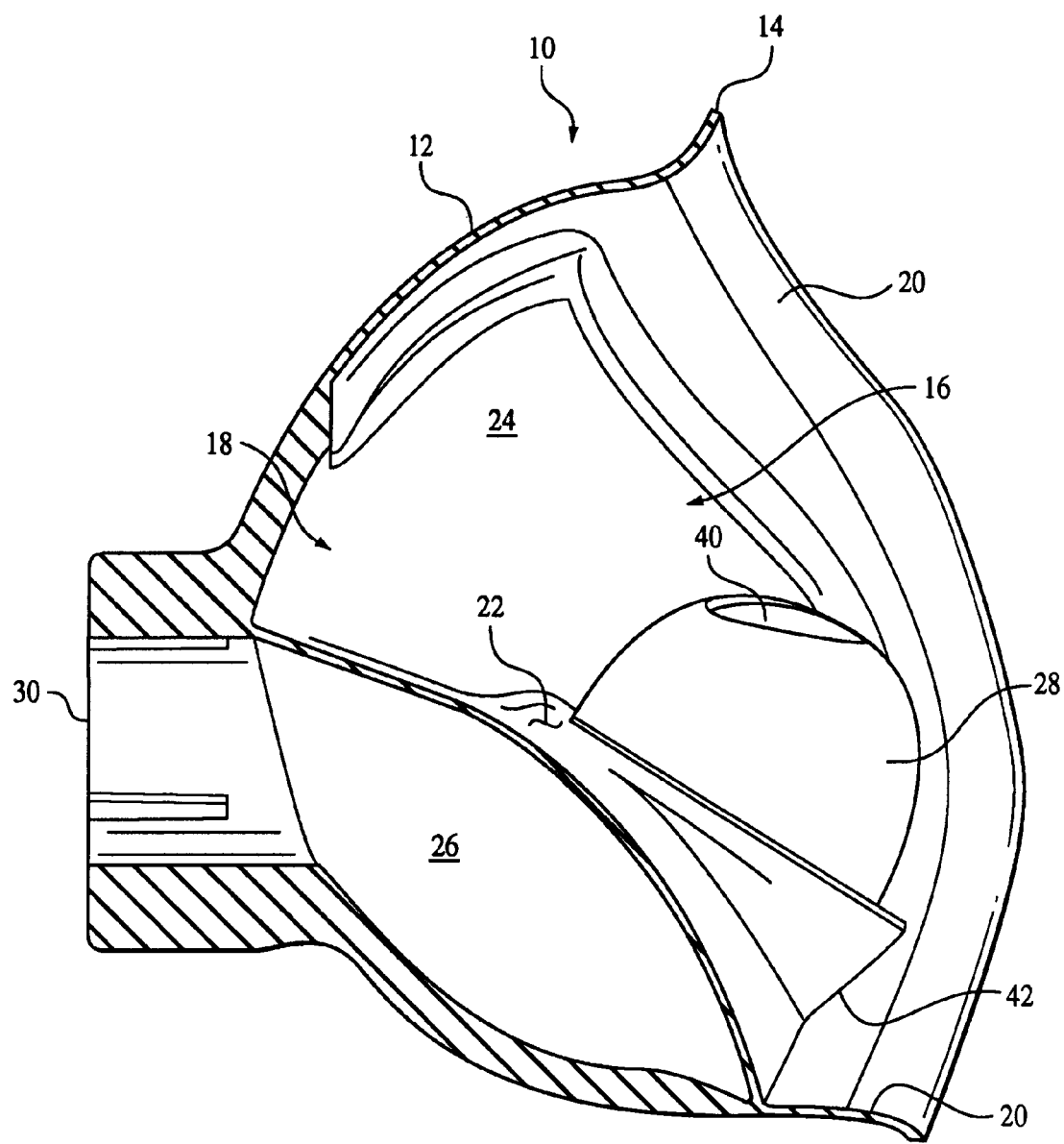
FIG. 5 is a section taken along line 5-5 in FIG. 4.
Figure 6:
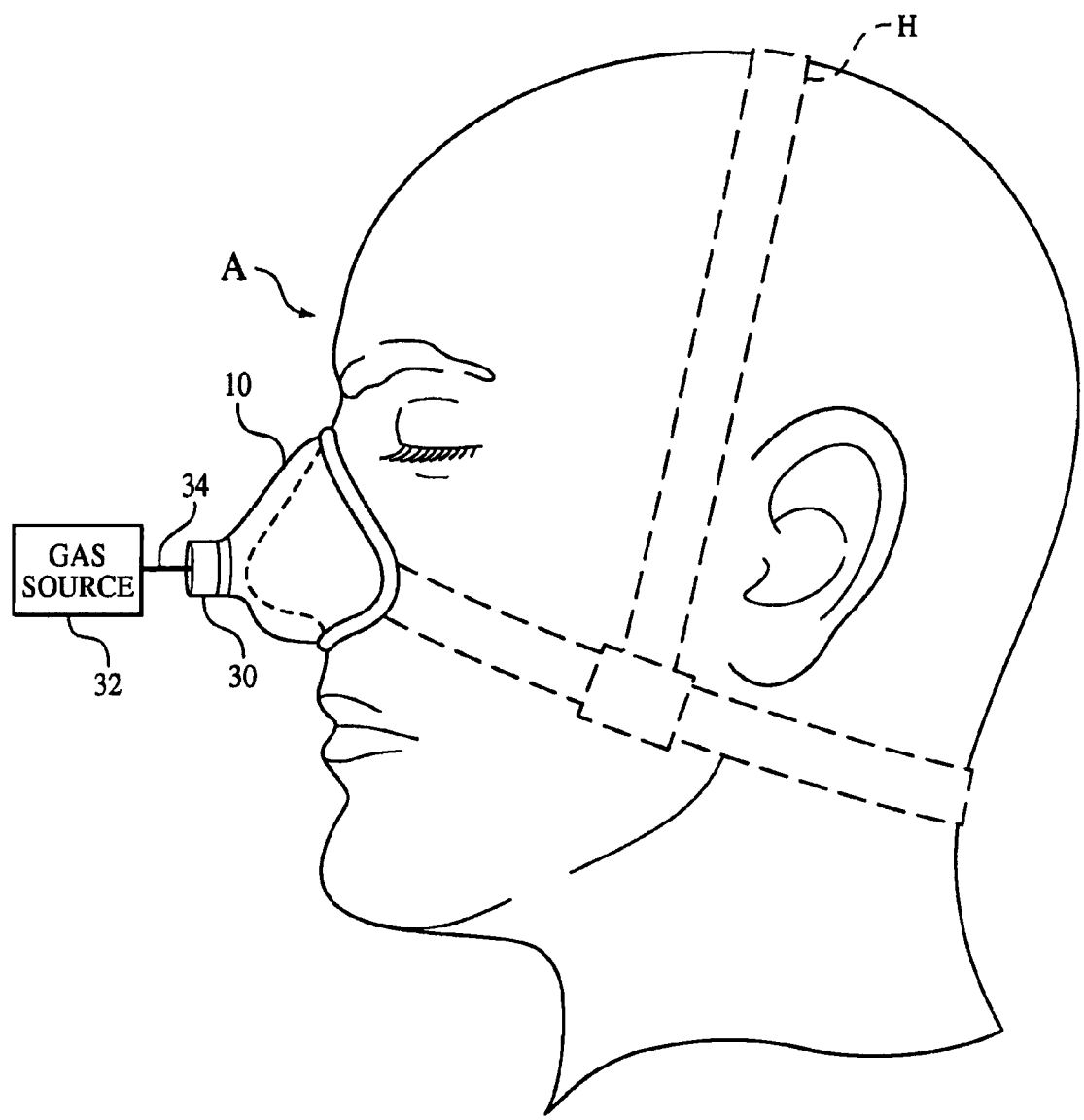
FIG. 6 is a view of the patient interface shown in FIG. 2 mounted operatively on the face of a patient.

With reference to FIG. 5 and with continuing to reference to FIGS. 2-4, patient interface 10 includes a partition 22 that separates interior 18 into a first chamber 24, configured to receive the nose of a patient, and a second chamber 26. Patient interface 10 further includes a pair of nasal pillows 28 integral with partition 22 and projecting therefrom into first chamber 24 for full, or partial, insertion into the nares of a patient when patient interface 10 is mounted operatively on a face A of the patient as shown in FIG. 6.

Patient interface 10 includes an integral port 30 in fluid communication with second chamber 26 for delivery of gas to and from the patient via nasal pillows 28. The gas provided to the patient can be any suitable breathing gas known in the art. The gas is provided to the patient via a gas source 32 and a gas delivery hose 34.

Figure 7:
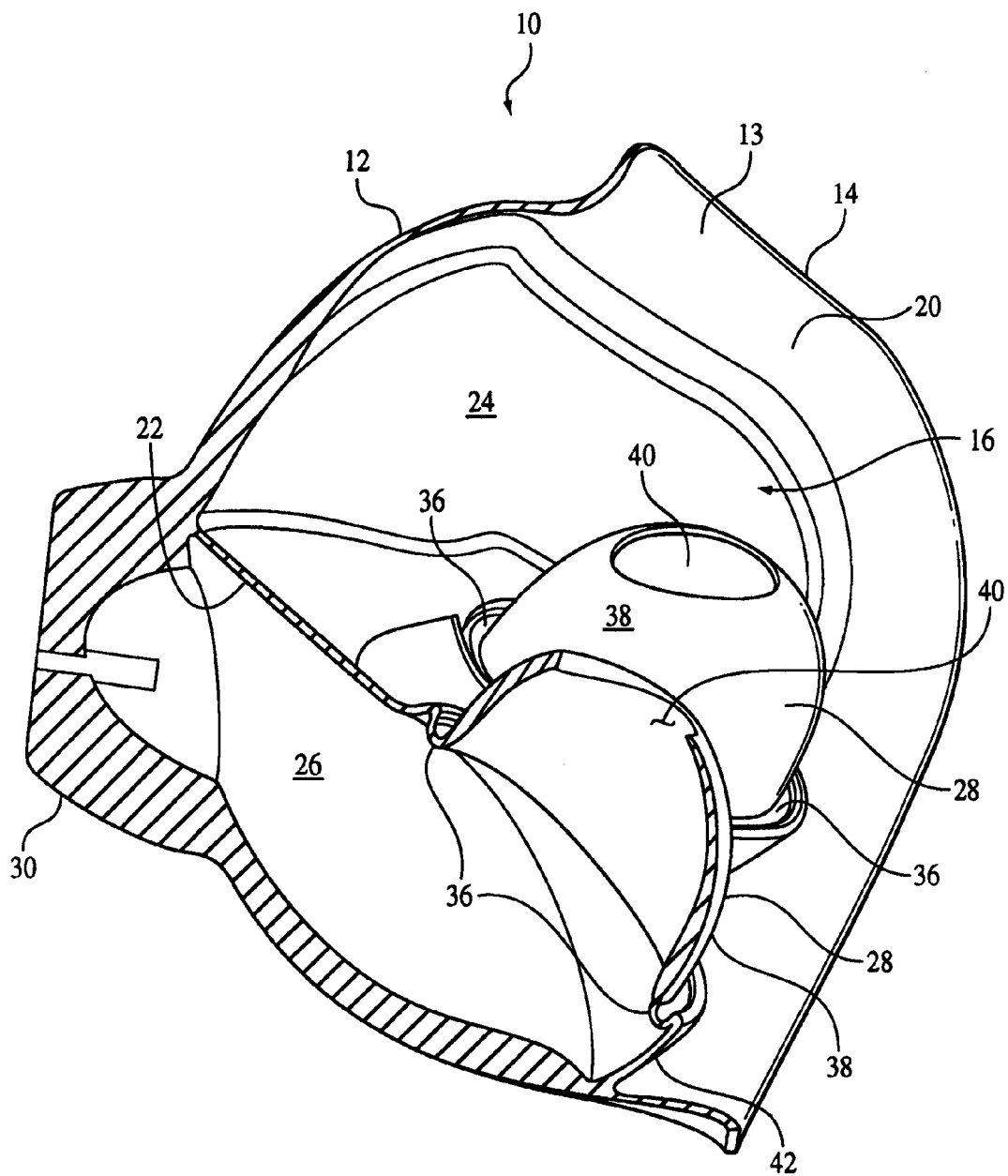
FIG. 7 is a section taken along lines 6-6 in FIG. 4.

With reference to FIG. 7 and with continuing reference to all previous figures, patient interface 10 includes a bellows 36 between each nasal pillow 28 and partition 22. Each bellows 36 moveably couples its corresponding nasal pillow 28 to partition 22. As shown in FIG. 7, the bellows is a rolling diaphragm; however, various other configurations could be used without departing from the scope of the present invention. Each bellows 36 enables its corresponding nasal pillow 28 to move in order to facilitate alignment and insertion into the nare, or nasal cavity, of the patient. Desirably, each nasal pillow 28 has an elliptical, dome-shaped portion 38 with an opening 40 at the apex thereof. However, this is not to be construed as limiting the invention. Various other geometric shapes could be used without departing form the scope of the present invention.

As shown best in FIGS. 5 and 7, partition 22 slopes from a position above port 30 to a position adjacent a bottom of opening 16. Desirably, other than openings 40 at the apices of nasal pillows 28, partition 22 forms a substantially gas tight seal between first chamber 24 and second chamber 26, whereupon the exclusive path for the passage of gas therebetween is via openings 40.

Adjacent opening 16, partition 22 can include a pair of oval-shaped rims 42, each of which supports a corresponding bellows 36 and nasal pillow 28 in an operative position for insertion of the elongated dome shape of the nasal pillow 28 in the oval-shaped nostril of the patient when patient interface 10 is mounted operatively on face A of the patient. For example, as shown best in FIG. 5, the height of each rim 42 can be greatest adjacent opening 16 and can decrease in height with increasing distance from opening 16.

Figure 9:
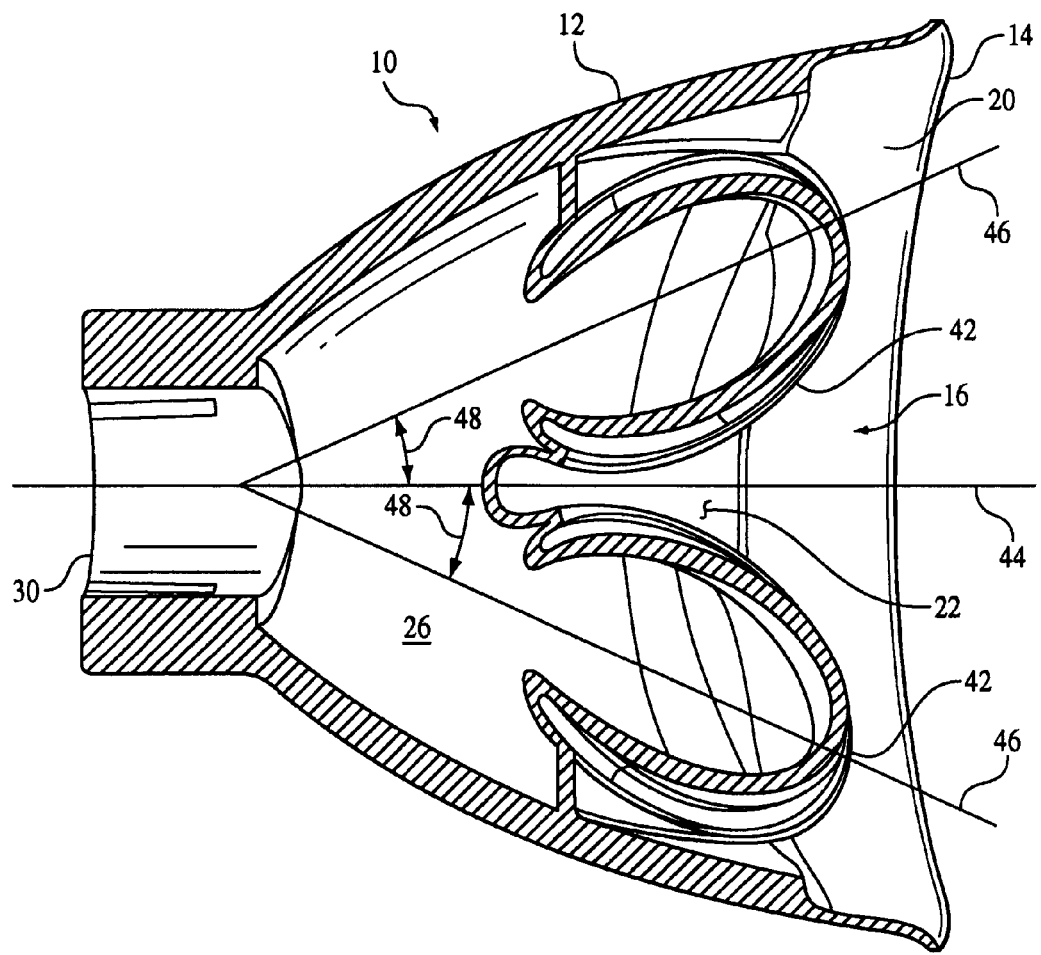
FIG. 9 is a section taken along lines 9-9 in FIG. 8.

In addition, or alternatively, if desired, the height of each rim 42 adjacent a side of shell portion 12 can be greater than the height of the rim 42 adjacent a longitudinal axis 44 of patient interface 10, shown best in FIG. 9. This difference in height causes the corresponding nasal pillow 28 to incline inwardly toward longitudinal axis 44 thereby further facilitating insertion of the elliptical domed portion 38 of the nasal pillow 28 in the substantially elliptically-shaped nares of the patient when patient interface 10 is mounted operatively on face A of the patient.

As best appreciated by one of ordinary skill in the art, a benefit of each rim 42 is that it facilitates desirable positioning of the corresponding bellows 36 and nasal pillow 28 to the elliptically-shaped nare of the patient when patient interface 10 is mounted operatively on face A of the patient. The foregoing description of partition 22, rim(s) 42 and one or both bellows 36, however, is not to be construed as limiting the invention since it is envisioned that the functions of one more of these elements can realized in a multitude of suitable and desirable manners. For example, each rim 42 can be omitted and the lower portion of each nasal pillow 28 modified to perform the positioning function of the omitted rim 42, e.g., the lower portion of each nasal pillow 28 can be extended downwardly in the form of the omitted rim 42. Where a nasal pillow 28 is modified in this manner, the corresponding bellows 36 is coupled between partition 22 and the downwardly extended lower portion of the modified nasal pillow 28.

Figure 8:
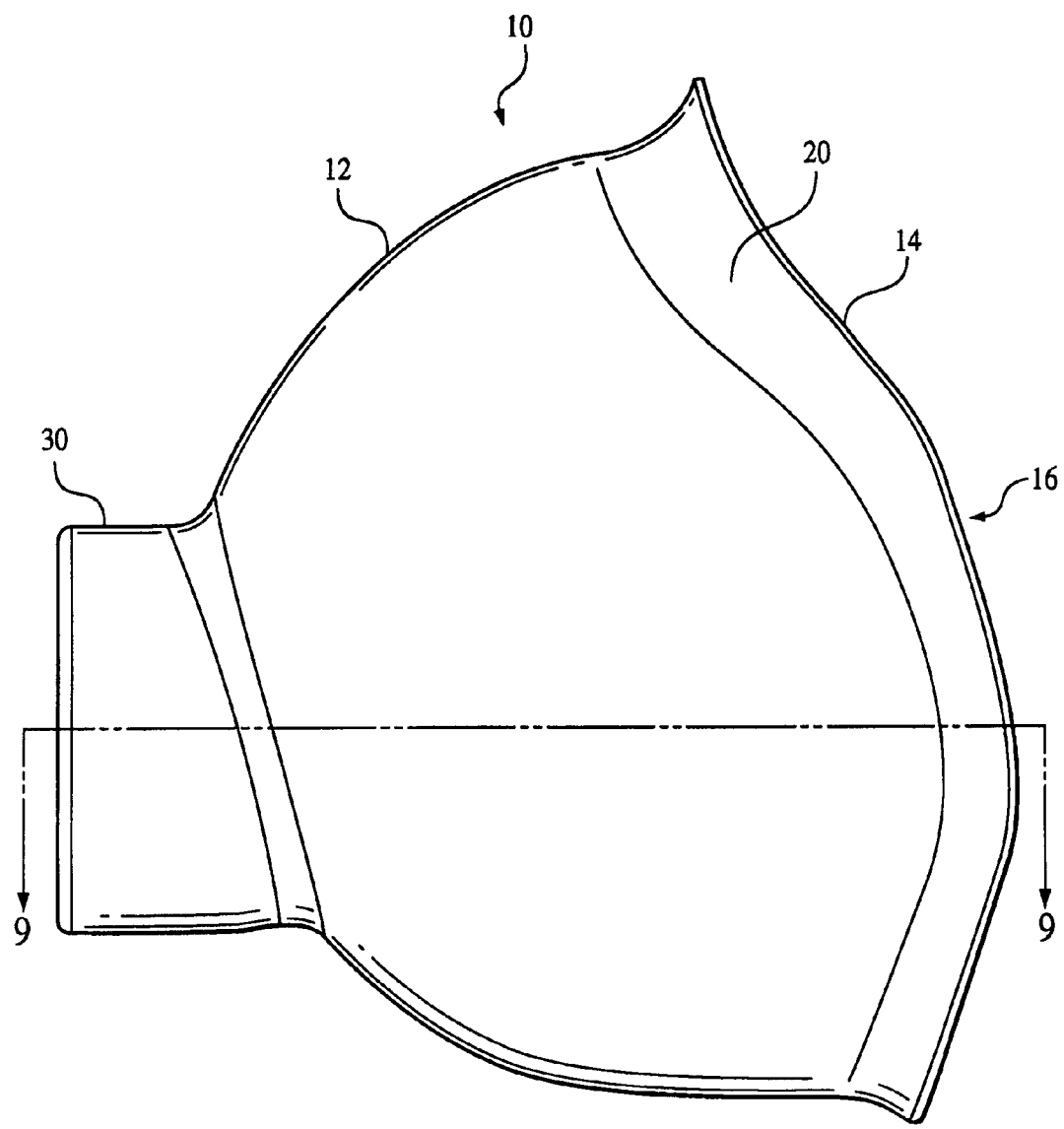
FIG. 8 is a side view of the patient interface shown in FIG. 2.

With reference to FIGS. 8 and 9 and with continuing reference to all previous figures, a longitudinal axis 46 of each nasal pillow 28 is positioned at an angle 48 with respect to longitudinal axis 44 of patient interface 10. The combination of the angle 48 such that each nasal pillow 28 is angled outward, the rims 42 that angle the nasal pillows 28, the elliptical-domed portion 38 of each nasal pillow 28 that conforms to the patients nares, and the action of bellows 36 enable each nasal pillow 28 to fit snuggly, desirably fluid tight, in the nostril of the patient when patient interface 10 is mounted operatively on face A of the patient. Desirably, each bellows 36 biases its corresponding nasal pillow 28 into a nostril of the patient when the patient interface is mounted operatively on the face of the patient. However, this is not to be construed as limiting the invention.

Figure 10:
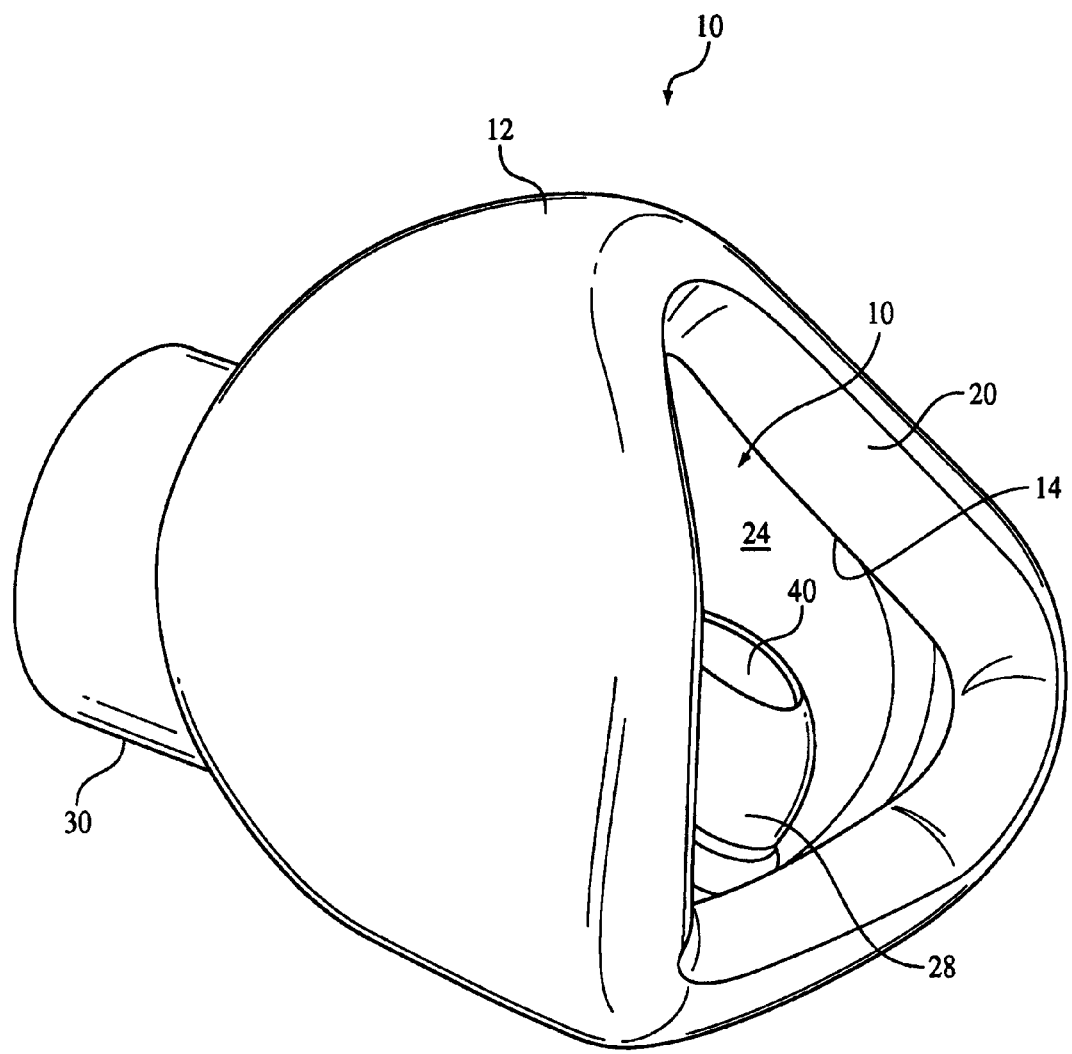
FIG. 10 is a perspective view of a patient interface in accordance with another embodiment of the present invention.
Figure 11:
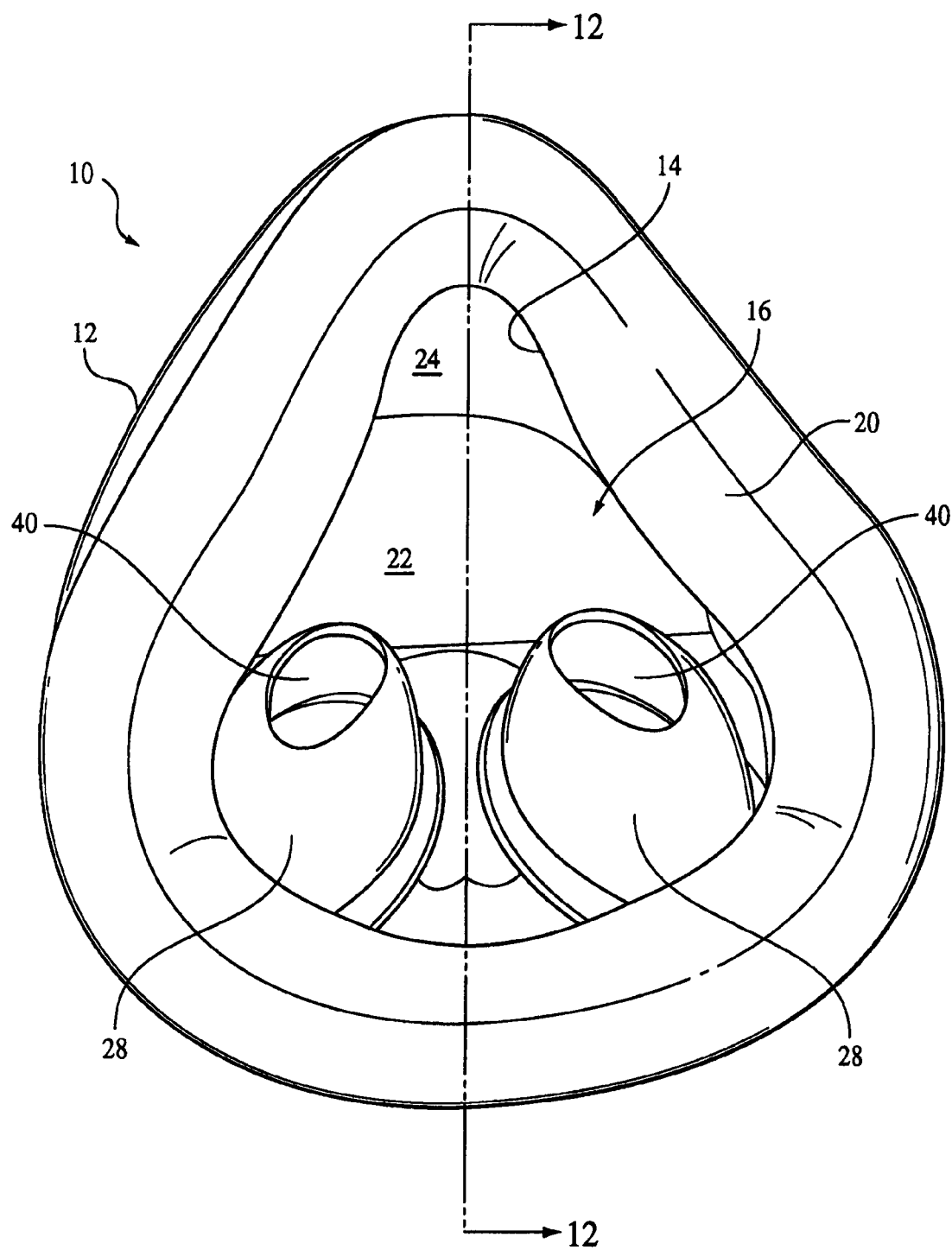
FIG. 11 is a view of the open end of the patient interface shown in FIG. 9.
Figure 12:
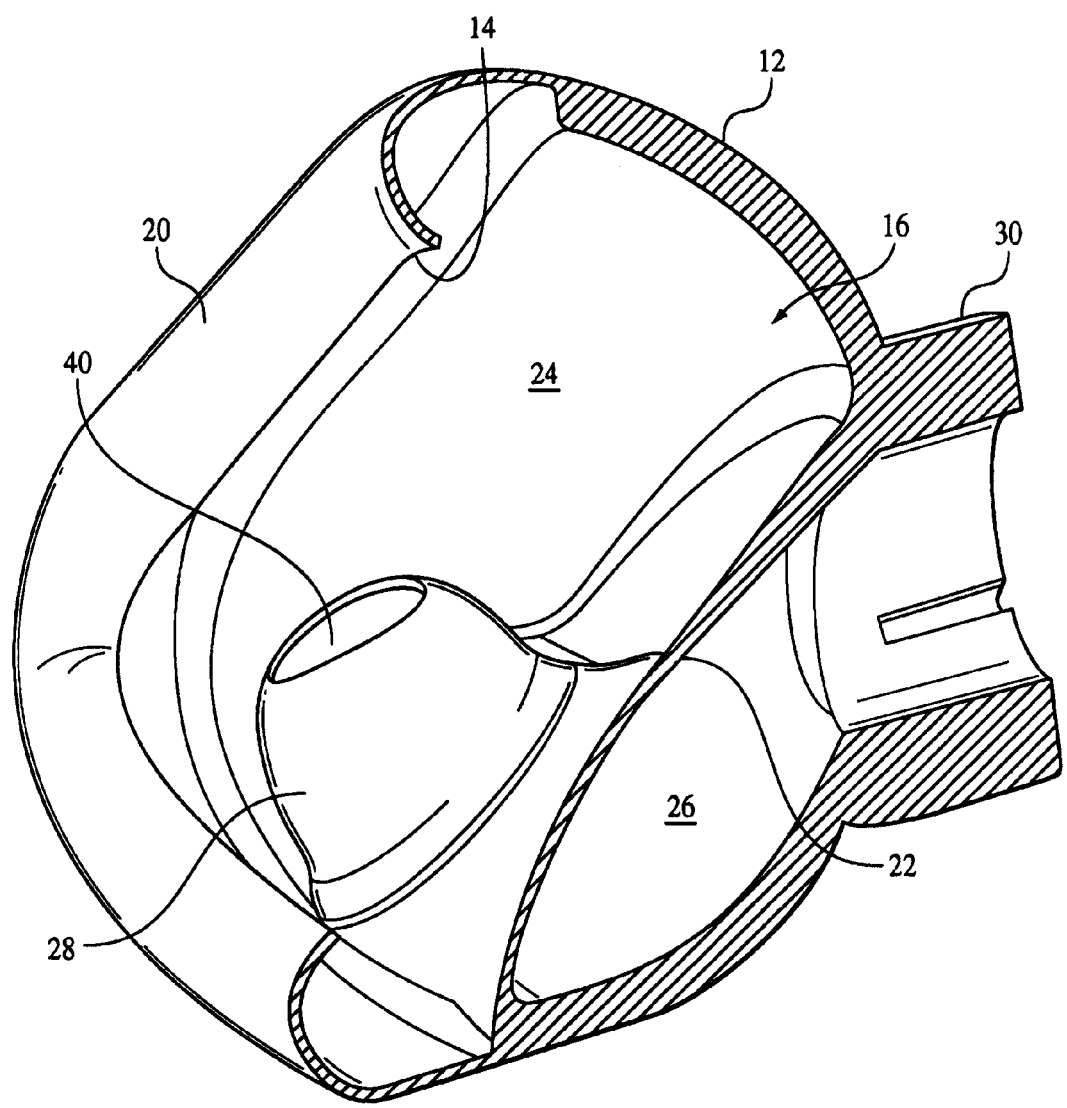
FIG. 12 is a section taken along lines 12-12 in FIG. 11.

With reference to FIGS. 10-12 and with continuing reference to all previous figures, in an alternate embodiment of patient interface 10, the flange 20 rolls or curves inwardly into first chamber 24 such that peripheral edge 14 faces into first chamber 24. This is in contrast to the embodiment of patient interface 10 shown in FIGS. 2-9, wherein flange 20 flares outwardly away from first chamber 24. Other than flange 20 flaring outwardly away from first chamber 24 in FIGS. 2-9 and flange 20 rolling inwardly into first chamber 24 in FIGS. 10-12, the embodiment of patient interface 10 shown in FIGS. 10-12 is similar to the embodiment of patient interface 10 shown in FIGS. 2-9. Accordingly, additional detailed description of the embodiment of patient interface 10 shown in FIGS. 10-12 will not be included herein to avoid unnecessary redundancy.

As can be seen, the present invention is a one-piece or unitary patient interface for use by a patient. The patient interface can be formed by any suitable process for forming a unitary structure such as injection molding, rotational molding, blow molding, etc. The patient interface is desirably made from a suitable biocompatible material that is resilient upon completion of the manufacturing process. Desirably, flange 20 and/or nasal pillows 28 of each embodiment of patient interface 10 discussed above are more resilient than the remaining portions of the unitary structure for patient comfort and to facilitate forming suitable fluid tight seal(s) with the face and/or nostrils of the patient when in use. However, the formation of fluid tight seals by nasal pillows 28 and/or flange 20 with the nostrils and/or face, respectively, of the patient is not to be construed as limiting the invention since it is envisioned that one or both of such fluid tight seal(s) is/are not required in use of either embodiment of patient interface 10.

The patient interface 10 described above can be mounted operatively on face A of the patient in any suitable manner. One example of a suitable means for mounting either embodiment of patient interface 10 operatively on face A of a patient is disclosed in U.S. Pat. No. 6,651,663 to Barnett et al., which is incorporated herein by reference. The Barnett et al. patent discloses a collar that can be mated with a patient interface which includes a plurality of cutouts that function as headgear attachment points for securing a headgear to collar. The embodiment of collar shown in the Barnett et al. patent includes three cutouts for headgear attachment points. However, this is not to be construed as limiting the invention since the number of headgear attachment points can be any desirable number, such as, without limitation, two or four. Another means for mounting either embodiment of patient interface 10 operatively on face A of a patient is disclosed in FIGS. 22A-22C and the corresponding description of U.S. Patent Application Publication No. US 2005/0076913 to Ho et al., which is also incorporated herein by reference. Since various means for attaching either embodiment of patient interface 10 operatively on face A of the patient are well known in the art, for purpose of simplicity, these means, as well as any other means for attaching patient interface 10 operatively on face A of the patient, will be denoted herein by the headgear H shown in FIG. 6.

One unique feature of the present invention is that the patient interface includes both a cushion portion 13 that fits about the patient's nose with nasal pillows 28 that fit within the patient's nares. This unique configuration separates the function of stabilizing the patient interface from the function of creating a seal between the patient and the patient interface 10. The cushion operates to stabilize and secure the mask in place and has a generally pyramidal-shape. In the event that forces are exerted longitudinally along the axis through port 30 towards the face A of the patient, the flange 20 will bear a majority of the applied forces rather than the nasal pillows 28. The region about the nares of a patient are well-known to be particularly sensitive. In prior designs, the nasal pillows often concentrate an excessive amount of force in this sensitive region. In contrast, the present invention disperses these forces about the patient's nose, thus reducing discomfort. In prior patient interfaces using nasal pillows, the headgear assembly required a number of complicated features to properly locate the nasal pillows on the face of the patient. A complicated construction is not necessary in the present invention. The nasal pillows 28 are predominately responsible for maintaining a seal between the patient and the mask sufficient to deliver gas to the patient. In fact, in one alternative design, the inventor contemplates that it may be desirable to add vent holes in the first chamber 24 to vent steam thus further enhancing the comfort experienced by patients of the present invention. This can be achieved since the seal can be maintained within the second chamber 26 and nasal pillows 28.

In one aspect, the present invention is formed from a unitary construction thus minimizing the potential for parts to be lost. For instance, the nasal pillows are preferably integrally formed with the partition. Alternatively, the nasal pillows may be formed separately from the partition and adhered or otherwise joined to the mask. This would permit the patient to select a nasal pillow that is properly sized and shaped for the particular shape of the patient's nares or replaced should excessive wear occur. In either embodiment, the gas supplied to the patient is mixed in the second chamber 26 before being delivered to the patient via nasal pillows 28. This intermixing ensures that the same gas is delivered at the same pressure to both nostrils of the patient.

Still further, the present invention includes elliptical dome portions that fit within the patient's nares. This construction is more comfortable since it is substantially anatomically correct. It also provides a large seal along a length of the patient's nares while also minimizing interference with the airflow. In addition, the nasal pillows are mounted on bellows, or rolling diaphragm 36. This feature permits the nasal pillows 28 to passively conform to the particular patient's nasal features thus enhancing comfort and seal integrity.

Yet another advantage of the present invention is that in one embodiment flange 20 rolls outwardly rather than inwardly. Although either configuration will provide adequate support, rolling the flange 20 outwardly is particularly advantageous since this construction provides the patient with extra clearance for the nasal pillows 28.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface comprising:
an elastomeric member comprising an elastomeric flange configured to surround a nose of a patient, the flange configured to substantially support the patient interface on the face of the patient;
a partition that is elastomeric and integral with the member, the partition separating an interior of the member into (i) a first chamber that is formed by the partition and the flange, and that is configured to receive the nose of the patient and (ii) a second chamber that is formed by the partition and the flange;
a pair of nasal pillows integral with the partition and projecting therefrom into the first chamber for at least partial insertion into nostrils of the patient when the patient interface is mounted operatively on the face of the patient, wherein the nasal pillows communicate the second chamber with the nostrils of the patient; and
a port integral with the member in fluid communication with the second chamber for delivery of gas to and from the patient via the second chamber and the nasal pillows.

2. The patient interface of claim 1, further including means integral with each nasal pillow and with the partition for moveably coupling the nasal pillow to the partition.

3. The patient interface of claim 2, wherein each means for moveably coupling biases its corresponding nasal pillow into one of the nostrils of the patient when the patient interface is mounted operatively on the face of the patient.

4. The patient interface of claim 1, wherein each nasal pillow has an opening at an apex thereof.

5. The patient interface of claim 1, further comprising a cushion disposed on a portion of the flange that contacts the face of the patient when the patient interface is mounted operatively on the face of the patient.

6. The patient interface of claim 5, wherein the cushion comprises one or both of a portion of the flange at the periphery of the flange that flairs outwardly away from the first chamber and/or a portion of the flange that rolls inwardly into the first chamber.

7. A patient interface comprising:
an elastomeric member defining an interior space, the member comprising an elastomeric flange configured to surround a nose of a patient, the flange configured to substantially support the patient interface on the face of the patient;
means for dividing the interior of the member into (i) a first chamber that is formed by the flange and the means for dividing, and that is configured to receive the nose of the patient and (ii) a second chamber that is formed by the flange and the means for dividing, wherein the means for dividing is elastomeric;
means projecting from the dividing means into the first chamber for delivery of gas to and from at least one nostril of the patient, wherein the means for delivery of gas communicates the second chamber with the nostrils of the patient; and
means in fluid communication with the second chamber for delivery of the gas to and from the patient via the second chamber and the delivery means.

8. The patient interface of claim 7, further including means for biasing the delivery means toward the at least one nostril of the patient when the patient interface is mounted operatively on the face of the patient with the nose of the patient in the first chamber.

9. The patient interface of claim 8, wherein the biasing means biases the delivery means into fluid tight relation with the at least one nostril of the patient.

10. The patient interface of claim 7, wherein the delivery means forms a fluid tight seal with the at least one nostril of the patient.

11. The patient interface of claim 7, further comprising a cushion disposed on a portion of the flange that contacts the face of the patient when the patient interface is mounted operatively on the face of the patient with the nose of the patient in the first chamber.

12. The patient interface of claim 11, wherein the cushion forms a fluid tight seal with the face of the patient when the patient interface is mounted operatively on the face of the patient.

13. The patient interface of claim 11, wherein the cushion comprises a portion of the flange at the periphery of the flange that flares outwardly away from the first chamber.

14. The patient interface of claim 11, wherein the cushion comprises a portion of the flange formed at the periphery of the flange that rolls inwardly into the first chamber.

15. The patient interface of claim 7, wherein the delivery means includes a pair of dome-shaped structures that extend into the first chamber, each dome-shaped structure having an opening at an apex thereof for the passage of gas.

16. The patient interface of claim 7, wherein the member and the means for dividing are formed from a single niece of elastomeric material.

17. A patient interface comprising:
an elastomeric member comprising an elastomeric flange configured to surround the nose of a patient, the flange configured to substantially support the patient interface on the face of the patient;
at least one nasal pillow extending from the member to contact at least a portion of the patient's nasal region;
a port integral with the member in fluid communication with the nasal pillows; and
a collar formed from a rigid material, the collar being configured to be engaged by an apparatus that holds the collar in position with respect to the head of the patient, the collar being removably mated with the member so as to hold the member in place on the face of the patient if the collar is held in position with respect to the head of the patient.

18. The patient interface as recited in claim 17, wherein the nasal pillow abuts the patient's nose.

19. The patient interface of claim 17, wherein the nasal pillow extends at least partially into a nostril of a patient.

20. The patient interface of claim 17, further comprising a cushion disposed on a portion of the flange that contacts the face of the patient when the patient interface is mounted operatively on the face of the patient.

21. The patient interface of claim 17, wherein the cushion comprises one or both of a portion of the flange that flairs outwardly away from the first chamber and/or a portion of the flange that rolls inwardly.

22. The patient interface of claim 17, wherein if the collar is mated with the member, the collar surrounds the port.

23. The patient interface of claim 14, wherein the member and the partition are formed entirely from a single piece of elastomeric material.

24. The patient interface of claim 23, wherein the member is configured to removably mate with a collar formed from a rigid material, the collar being configured to hold the member in place on the face of the patient.

25. The patient interface of claim 16, wherein the member is configured to removably mate with a collar formed from a rigid material, the collar being configured to hold the member in place on the face of the patient.

* * * * *